United States Patent
Marino et al.

(10) Patent No.: US 11,510,852 B2
(45) Date of Patent: Nov. 29, 2022

(54) METHOD FOR REVEALING RESIN-BASED COMPOSITES

(71) Applicant: THE ROYAL INSTITUTION FOR THE ADVANCEMENT OF LEARNING/MCGILL UNIVERSITY, Montréal (CA)

(72) Inventors: Faleh Tamimi Marino, Montréal (CA); Mohamed Nur Abdallah, Toronto (CA); Yara Oweis, Montréal (CA)

(73) Assignee: THE ROYAL INSTITUTION FOR THE ADVANCEMENT OF LEARNNG/MCGILL UNIVERSITY, Montreal (CA)

(*) Notice: Subject to any disclaimer, the term of this patent is extended or adjusted under 35 U.S.C. 154(b) by 281 days.

(21) Appl. No.: 16/865,643

(22) Filed: May 4, 2020

(65) Prior Publication Data
US 2020/0352829 A1 Nov. 12, 2020

Related U.S. Application Data

(60) Provisional application No. 62/844,158, filed on May 7, 2019.

(51) Int. Cl.
A61K 6/65 (2020.01)

(52) U.S. Cl.
CPC .................... A61K 6/65 (2020.01)

(58) Field of Classification Search
CPC ........................................... A61K 6/65
See application file for complete search history.

(56) References Cited

PUBLICATIONS

Tarle, Z. et al. "Contemporary Concepts on Composite Materials", Suvremene spoznaje o kompozitnim materijalima. 511(38) (2012) 23-38.
Tay, F.R. and Pashley, D.H. "Have dentin adhesives become too hydrophilic?". Journal-Canadian Dental Association 69(11) (2003) 726-732.
Topcu, F.T. et al. Influence of different drinks on the colour stability of dental resin composites, European journal of dentistry 3(1) (2009) 50-6.
Tüfekçi, E. et al. "Enamel loss associated with orthodontic adhesive removal on teeth with white spot lesions: an in vitro study". American Journal of Orthodontics and Dentofacial Orthopedics 125(6) (2004) 733-739.
Tyler, J.E. and Hardy, A.C. An analysis of the original Munsell color system, JOSA 30(12) (1940) 587-590.
Umasankar, Y. and Ramasamy, R.P. "Highly sensitive electrochemical detection of methyl salicylate using electroactive gold nanoparticles". Analyst 138(21) (2013) 6623-6631.
Varghese, H.T. et al. "IR, Raman and SERS studies of methyl salicylate". Spectrochimica Acta Part A: Molecular and Biomolecular Spectroscopy 66(4) (2007) 959-963.
Vlachojannis, C. et al. "Listerine® Products: an update on the efficacy and safety". Phytotherapy Research (2016).
Watts, A. and Addy, M. "Tooth discolouration and staining: Tooth discolouration and staining: a review of the literature". British dental journal 190(6) (2001) 309-316.

(Continued)

Primary Examiner — Benjamin J Packard
(74) Attorney, Agent, or Firm — Norton Rose Fulbright Canada LLP

(57) ABSTRACT

The present disclosure relates to a combination, a composite staining kit and a method for revealing a composite material on a tooth.

10 Claims, 18 Drawing Sheets

(56) References Cited

PUBLICATIONS

Xu, J. et al. "High-pressure infrared and FI—Raman investigation of a dental composite". Biomaterials 18(24) (1997) 1653-1657.

Yew, H.Z. et al. "A laboratory investigation of colour changes in two contemporary resin composites on exposure to spices". Australian dental journal 58(4) (2013) 468-477.

Zarrinnia, K. et al. "The effect of different debonding techniques on the enamel surface: An in vitro qualitative study". American Journal of Orthodontics and Dentofacial Orthopedics 108(3) (1995) 284-293.

Dozic, A. et al. "Performance of five commercially available tooth color-measuring devices". Journal of prosthodontics : official journal of the American College of Prosthodontists 16(2) (2007) 93-100.

Eimar, H. et al. "Hydrogen peroxide whitens teeth by oxidizing the organic structure". Journal of Dentistry 40 (2012) e25-e33.

Finer, Y. and Santerre, J. "The influence of resin chemistry on a dental composite's biodegradation". J. Biomed. Mater. Res., Part A 69(2) (2004) 233-246.

Ghadimi, E. et al. "Trace elements can influence the physical properties of tooth enamel". SpringerPlus 2(1) (2013) 499.

Gracco, A. et al. "SEM-Evaluation of enamel surfaces after orthodontic debonding: a 6 and 12-month follow-up in vivo study" Scanning 37(5) (2015) 322-326.

Guler, A.U. et al. "Effects of different drinks on stainability of resin composite provisional restorative materials". The Journal of prosthetic dentistry 94(2) (2005) 118-124.

Hermanson, A.S. et al. "Ultraviolet Illumination as an Adjunctive Aid in Dental Inspection*". Journal of Forensic Sciences 53(2) (2008) 408-411.

Hosein, M et al. "Enamel loss during bonding, debonding, and cleanup with use of a self-etching primer". American Journal of Orthodontics and Dentofacial Orthopedics 126(6) (2004) 717-724.

Reland, A.J. et al. "Enamel loss at bond-up, debond and clean-up following the use of a conventional light-cured composite and a resin-modified glass polyalkenoate cement". European Journal of Orthodontics 27(4) (2005) 413-41.

Johnston, W.M. "Color measurement in dentistry". Journal of Dentistry 37 (2009) e2-e6.

Joiner, A. et al. "Adsorption from black tea and red wine onto in vitro salivary pellicles studied by ellipsometry". European journal of oral sciences 111(5) (2003) 417-422.

Kim, S.-S. et al. "Enamel surface evaluation after removal of orthodontic composite remnants by intraoral sandblasting: A 3-dimensional surface profilometry study". American Journal of Orthodontics and Dentofacial Orthopedics 132(1) (2007) 71-76.

Kumari, R.V. et al. "Evaluation of the effect of surface polishing, oral beverages and food colorants on color stability and surface roughness of nanocomposite resins". Journal of international oral health: JIOH 7(7) (2015) 63.

Abd El-Hakam Abou El-Nasr, E. et al. "Infrared and ultraviolet laser spectroscopy of jet-cooled substituted salicylic acids; substitution effects on the excited state intramolecular proton transfer in salicylic acid". Molecular Physics 103(11-12) (2005) 1561-1572.

Abdallah, M.-N. et al. "Development of a composite resin disclosing agent based on the understanding of tooth staining mechanisms" Journal of Dentistry 42(6) (2014) 697-708.

Azer, S.S. et al. "Effect of pH on tooth discoloration from food colorant in vitro". Journal of dentistry 38, Supplement 2 (2010) e106-e109.

Baka, E. et al. "Study of equilibrium solubility measurement by saturation shake-flask method using hydrochlorothiazide as model compound". Journal of pharmaceutical and biomedical analysis. 46(2) (2008) 335-341.

Barutcigil, ç. and Yildiz, M. "Intrinsic and extrinsic discoloration of dimethacrylate and silorane based composites". Journal of dentistry 40, Supplement 1 (2012) e57-e63.

Belsito, D. et al. A toxicologic and dermatologic assessment of salicylates when used as fragrance ingredients, Food and Chemical Toxicology 45(1) (2007) S318-S361.

Benthaus, S. et al. "A new technique for the postmortem detection of tooth-coloured dental restorations", International Journal of Legal Medicine 111 (3) (1998) 157-159.

Berzina-Cimdina, Land Borodajenko, N. "Research of calcium phosphates using Fourier transform infrared spectroscopy". INTECH Open Access Publisher 2012.

Briggs, D. et al. XPS studies of the Oxygen 1s and 2s Levels in a Wide Range of Functional Polymers. Analytical Chemistry 65(11) (1993) pp. 1517-1523.

Brożyna, A. et al. "Different Susceptibility of Cells of Porcine Skin and Internal Organs to Ultraviolet A—Induced Breaking of Nuclear DNA". Photochemistry and Photobiology 81(3) (2005) 674-681.

Campbell, P.M. "Enamel surfaces after orthodontic bracket debonding", The Angle orthodontist 65(2) (1995) 103-110.

Carson, D.O. et al. "Detection of white restorative dental materials using an alternative light source". Forensic Science International 88(2) (1997) 163-168.

Cenci, M. et al. "The effect of polishing techniques and time on the surface characteristics and sealing ability of resin composite restorations after one-year storage". Operative dentistry 33(2) (2008) 169-176.

Chastain, J. et al. "Handbook of X-ray photoelectron spectroscopy: a reference book of standard spectra for identification and interpretation of XPS data" Physical Electronics Eden Prairie, MN1995.

Chowdhary, Z. et al. "Disclosing Agents In Periodontics: An Update, Journal of Dental College Azamgarh". Available at: http://nebula.wsimg. com/5d867182ab0040f0f175ee9bef4988b7.

Chu, S.J. et al. "Dental color matching instruments and systems. Review of clinical and research aspects". Journal of Dentistry 38, Supplement 2 (2010) e2-e16.

Lapczynski, L. et al. "Fragrance material review on methyl salicylate". Food and chemical toxicology 45(1) (2007) S428-S452.

López, G.P. et al. XPS O 1s binding energies for polymers containing hydroxyl, ether, ketone and ester groups, Surface and Interface Analysis vol. 17(5) (1991) pp. 267-272.

Mason, L. et al. "Systematic review of efficacy of topical rubefacients containing salicylates for the treatment of acute and chronic pain". BMJ : British Medical Journal 328(7446) (2004) 995-995.

McCarthy, S.J. et al. "In-vivo degradation of polyurethanes: transmission-FTIR microscopic characterization of polyurethanes sectioned by cryomicrotomy". Biomaterials 18(21) (1997) 1387-409.

McGuire, R.G. "Reporting of objective color measurements". HortScience 27(12) (1992) 1254-1255.

Meller, C. and Klein, C. "Fluorescence properties of commercial composite resin restorative materials in dentistry". Dental materials journal 31(6) (2012) 916-923.

Merza, M.Y. and El-Bermani, M.F. "Estimations of excited state dipole moments of conformers in some o-substituted acetophenones by solvato-chromic shifts". Spectrochimica Acta Part A: Molecular and Biomolecular Spectroscopy 60(7) (2004) 1677-1683.

Nathoo, S.A. "The chemistry and mechanisms of extrinsic and intrinsic discoloration". The Journal of the American Dental Association 128 (1997) 6S-10S.

Paravina, R.D. et al. "Teaching of color in predoctoral and postdoctoral dental education in 2009". Journal of dentistry 38 (2010) e34-e40.

Qamar, Z. et al. "Influence of Trace elements on dental enamel properties: A review". J Pak Med Assoc. vol. 67, No. 1. (2017).

Ren, Y.-F. et al. "Effects of common beverage colorants on color stability of dental composite resins: the utility of a thermocycling stain challenge model in vitro". Journal of dentistry 40 (2012) e48-e56.

Satou, N. et al. "In vitro color change of composite-based resins" Dental Materials 5(6) (1989) 384-387.

Seskar, M. et al. "Endogenous methyl salicylate in pathogen-inoculated tobacco plants". Plant Physiology 116(1) (1998) 387-392.

Stober, T. et al. "Color stability of highly filled composite resin materials for facings". Dental Materials 17(1) (2001) 87-94.

Tani, K. et al. "Discrimination between Composite Resin and Teeth using Fluorescence Properties". Dental materials journal 22(4) (2003) 569-580.

(56) References Cited

PUBLICATIONS

Ertas, E. et al. "Color stability of resin composites after immersion in different drinks". Dental materials journal 25(2) (2006) 371-376.
Fujita, M. et al. "Color change of newly developed esthetic restorative material immersed in food-simulating solutions". Dental materials journal 25(2) (2006) 352-359.
Mamura, S. et al. "Effect of filler type and polishing on the discoloration of composite resin artificial teeth", Dental materials journal 27(6) (2008) 802-808.
Omata, Y. et al. "Staining of hybrid composites with coffee, oolong tea, or red wine". Dental materials journal 25(1) (2006) 125-131 Inventors.
Trivedi, M.K. "Fourier Transform Infrared and Ultraviolet-Visible Spectroscopic Characterization of Treated Salicylic Acid and Sparfloxacin". Natural Products Chemistry & Research-Open Access 3(5) (2015).

METHOD FOR REVEALING RESIN-BASED COMPOSITES

CROSS-REFERENCE TO RELATED APPLICATION

This applications claims benefit of U.S. provisional application 62/844,158 filed on May 7, 2019, the content of which is hereby incorporated by reference in its entirety.

FIELD OF THE DISCLOSURE

The present disclosure relates to a combination, a composite staining kit and a method for revealing a composite material on a tooth.

BACKGROUND OF THE DISCLOSURE

Resin-based composites are widely used in dentistry for many applications due to their excellent esthetic and mechanical properties. Since the introduction of composite resin as an esthetic adhesive material, many improvements have been made focusing mainly on deceasing their polymerization shrinkage, improving their compressive strength, wear resistance and esthetic properties.

Beneficial properties (such as a more natural look and resistance to staining) for the patients might cause significant problems to the dentist once these materials require removal or replacement in case of broken restorations, recurrent caries formation or after the termination of orthodontic treatments when brackets are de-bonded and residual composite on enamel surface is removed. This procedure needs meticulous attention to minimize inadvertent iatrogenic enamel loss which is mainly due to the high resemblance of composite to the natural enamel surface. In fact, with constant improvement of composite resin material, visual inspection under conventional illumination is becoming more difficult and not reliable. Iatrogenic removal of sound enamel after orthodontic de-bonding, results in the tooth becoming more prone to discoloration, sensitivity and caries formation, besides affecting its esthetic properties. On the other hand, incomplete removal of the resin adhesive can result in a trap for plaque retention which causes discoloration to the tooth and difficulty for patients to maintain oral hygiene.

Several methods have been suggested to clean up composite remnants after bracket removal. All techniques reported produced different degrees of polish and some introduced abrasion anomalies accompanied by a significant loss of enamel height. Those problems are sometimes technique related but to a considerable extent are due to the high resemblance of composite resin to tooth enamel.

Another difficulty arises in locating the exact boundaries of the resin cement and verifying that all resin adhesive was removed from the enamel surface. Tactile difference in surface quality has been used as a detection method to discriminate composite from tooth structure, however, this method cannot be considered reliable as it is highly dependent on the dentist's skills and experience.

Curcumin, was used in the development of a staining protocol which gave visually acceptable results.

Although it was successful in staining composite and not the tooth structure, curcumin-based disclosing agent suffered a draw back; curcumin's solubility in 100% alcohol and thus cannot be used in the oral cavity. It is also soluble in oil, but this solvent cannot be used in dentistry as it leaves residues on the tooth surface which could interfere with the bonding of the new composite restoration.

Consequently, there exists a need for alternative methods to help the dentist in accurately identifying composite boundaries.

SUMMARY OF THE DISCLOSURE

A method of revealing a composite material comprising:
a. applying a phenolic residue-containing compound to the composite material; and
b. applying a staining agent after step a.

A composite staining kit comprising i) a phenolic residue-containing compound and ii) a staining agent wherein each of i) and ii) are in separate packaging or formulation.

A combination comprising i) a phenolic residue-containing compound and ii) a staining agent.

DETAILED DESCRIPTION OF THE DISCLOSURE

Figures 1A, 1B, 1C:
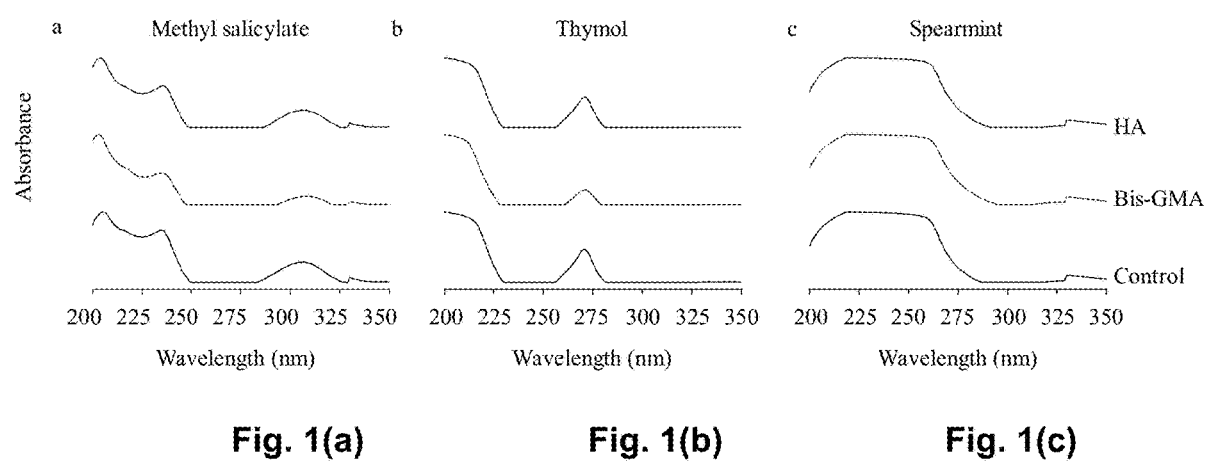
FIG. 1(a) is a UV visible absorbance spectrum of methyl salicylate analyzed, alone (control), or after the addition of 0.5 g Composite resin powder (Bis-GMA), or 0.5 g hydroxy-apatite powder (HA)
FIG. 1(b) is a UV visible absorbance spectrum of thymol analyzed, alone (control), or after the addition of 0.5 g Composite resin powder (Bis-GMA), or 0.5 g hydroxy-apatite powder (HA)
FIG. 1(c) is a UV visible absorbance spectrum of spearmint oil analyzed, alone (control), or after the addition of 0.5 g Composite resin powder (Bis-GMA), or 0.5 g hydroxy-apatite powder (HA)
Figure 2A:
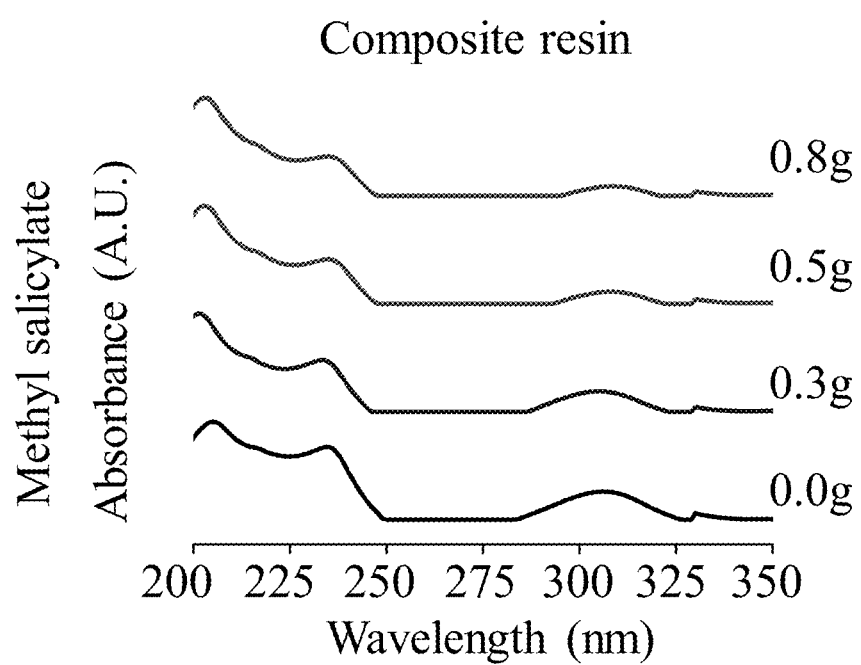
FIG. 2(a) is a UV visible spectrophotometer absorbance spectrum of methyl salicylate alone and after the addition of different weights (0.3, 0.5, 0.8 g) of composite resin.
Figure 2B:
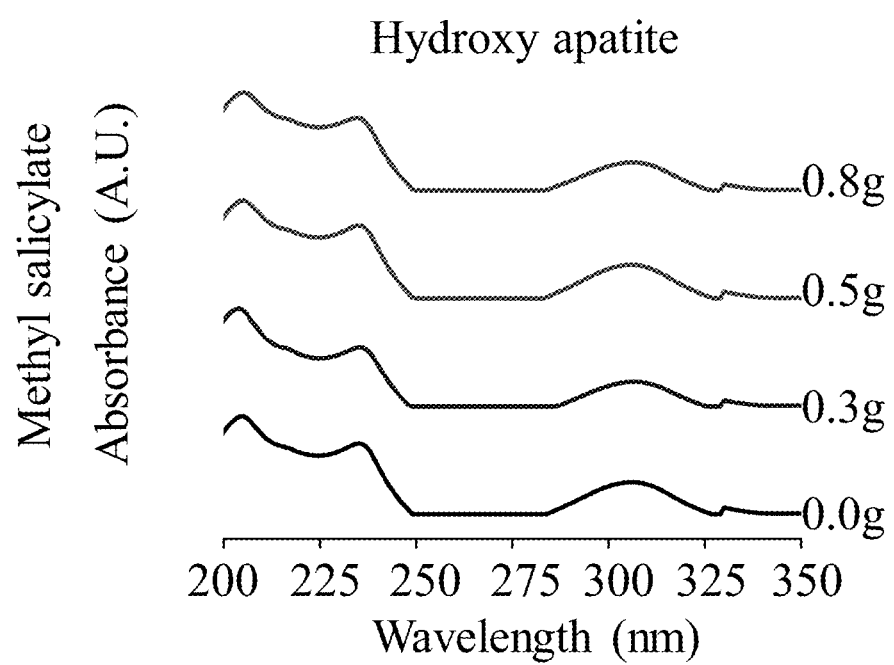
FIG. 2(b) is a UV visible spectrophotometer absorbance spectrum of methyl salicylate, alone and after the addition of different weights (0.3, 0.5, 0.8 g) of synthetic hydroxy-apatite (HA)
Figure 2C:
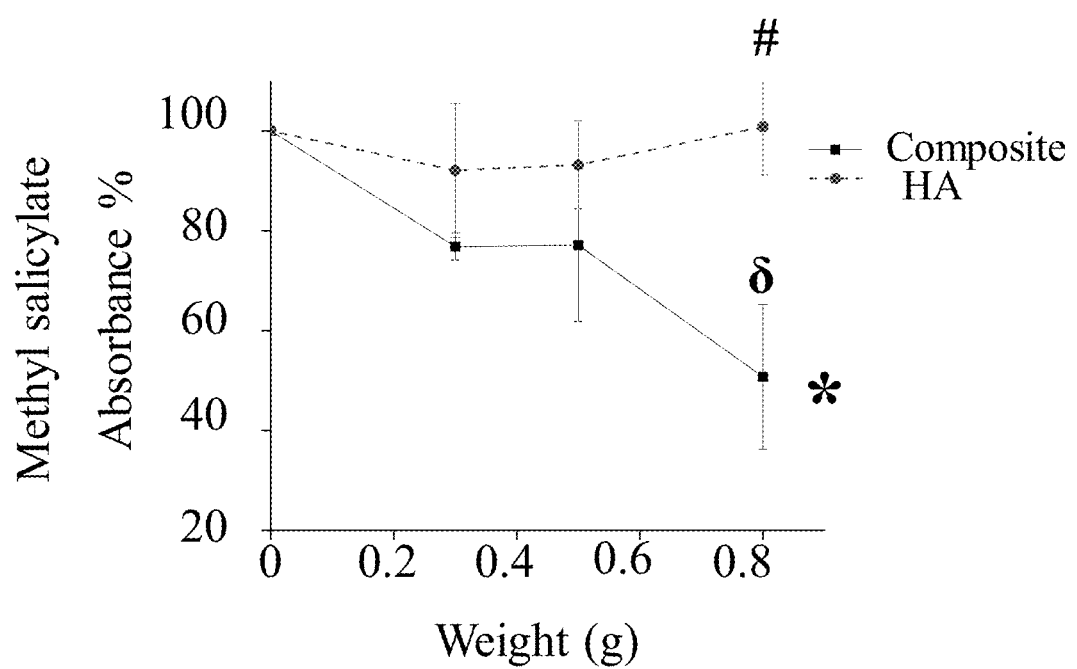
FIG. 2(c) is a scatter plot illustrating the change in the percentage of absorbance as a function of different weights of both composite resin and hydroxy-apatite for methyl salicylate.
Figure 2D:
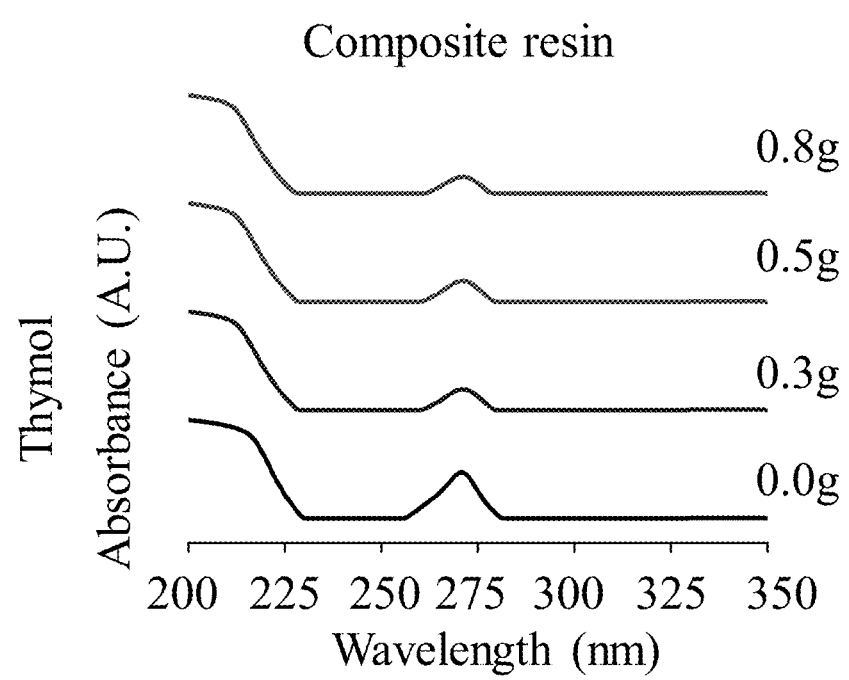
FIG. 2(d) is a UV visible spectrophotometer absorbance spectrum of thymol alone and after the addition of different weights (0.3, 0.5, 0.8 g) of composite resin.
Figure 2E:
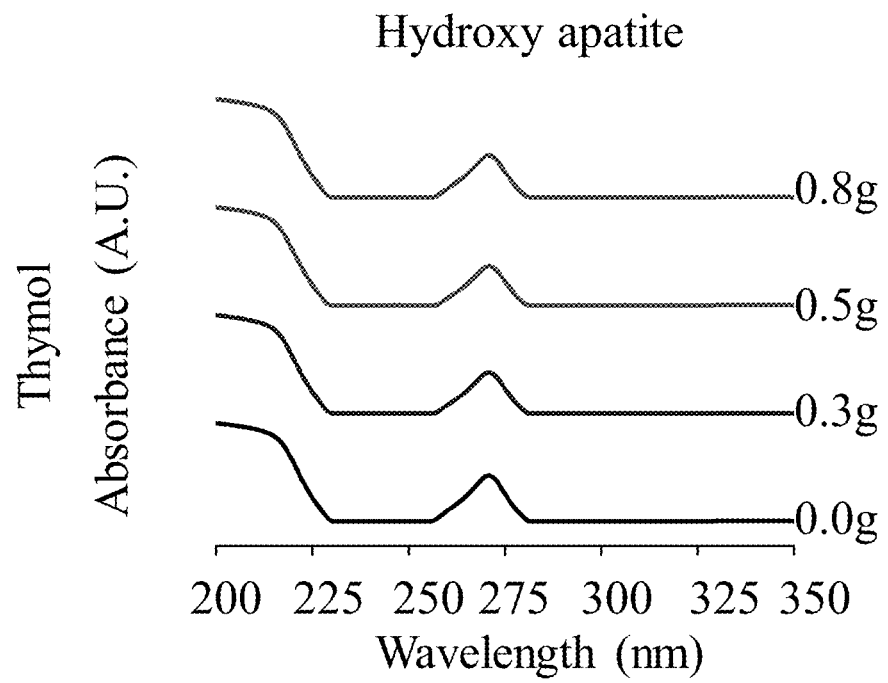
FIG. 2(e) is a UV visible spectrophotometer absorbance spectrum of thymol alone and after the addition of different weights (0.3, 0.5, 0.8 g) of synthetic hydroxy-apatite (HA)
Figure 2F:
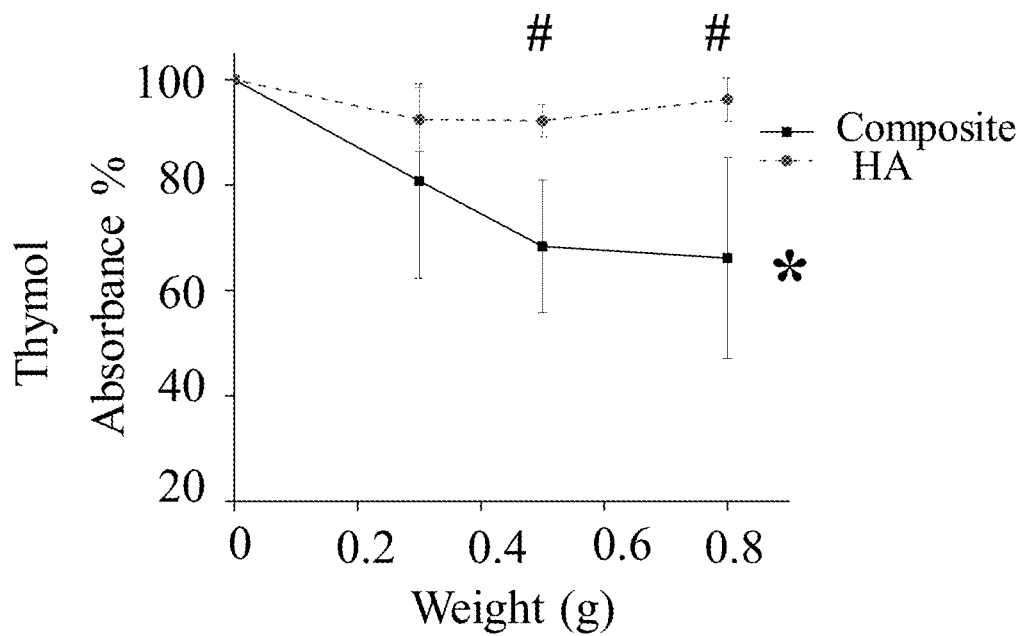
FIG. 2(f) is a scatter plot illustrating the change in the percentage of absorbance as a function of different weights of both composite resin and hydroxy-apatite for thymol (f)

The present disclosure relates to a combination, a composite staining kit and a method for revealing a composite material on a tooth in two steps comprising applying a phenolic residue-containing compound to the composite material and applying a staining agent. The process is intended to facilitate the complete removal of composite without inducing trauma to sound tooth structure.

In one embodiment, the combination of said i) a phenolic residue-containing compound and ii) a staining agent are in separate packaging or formulations.

In one embodiment of the method, the phenolic residue-containing compound is applied as a solution and dried before applying the staining agent.

In one embodiment of the method, the phenolic residue-containing compound is applied as a solution, dried, washed with water and dried again before applying the staining agent.

In one embodiment of the method, the staining agent is applied as a solution and dried.

In one embodiment of the method, the staining agent is applied as a solution, dried, washed with water and dried again.

Phenolic Residue-Containing Compound

In one embodiment, the phenolic residue-containing compound as used herein is preferably a mono-aromatic, topically non-toxic compound, especially a topically non-toxic compound for use in the mouth of a patient, and being non-toxic for natural tooth.

In one embodiment the phenolic residue-containing compound is in a form of a solution, preferably in a topically non-toxic alcoholic solution, such as an ethanol or isopropanol (preferably ethanol) solution (e.g. at room temperature—about 20-25 degrees Celsius).

In one embodiment the phenolic residue-containing compound is a compound preferably having one or more (or all) of the following properties: soluble in ethanol at room temperature, a MW of from about 90 to 220, a Log P of from about 1.4 to about 5.3.

In a preferred embodiment, the phenolic residue-containing compound as used herein is preferably a mono-aromatic, topically non-toxic compound in a form of an ethanolic solution, for use in the mouth of a patient, the compound being non-toxic for natural tooth and having one or more (or all) of the following properties: soluble in ethanol at room temperature, a MW of from about 90 to 220, and a Log P of from about 1.4 to about 5.3.

Non-limiting examples of phenolic residue-containing compound include methyl salicylate (MeSa), thymol and phenol.

Staining Agent

In one embodiment, the staining agent is preferably a food-grade dye.

In one embodiment the staining agent is an FDA approved product.

In one embodiment the staining agent is in a form of a solution, preferably an aqueous solution.

In one embodiment the staining agent is not substantially binding to hydroxy-apatite, for example when assessed visually.

In one embodiment the staining agent is preferably an FDA approved food-grade dye, in a form of a solution, preferably an aqueous solution, and the staining agent is not substantially binding to hydroxy-apatite when assessed visually.

Non-limiting examples of staining agent include methylene blue, Brilliant Blue FCF and Phloxine B.

Composite Material

In one embodiment, the composite material is a dental filling composite material or an orthodontic bonding resin for brackets comprising a polymer obtained from aromatic and/or aliphatic dimethacrylate monomers.

The dental composite material is known in the art and comprises a cross-linked polymeric resin matrix obtained from aromatic and/or aliphatic dimethacrylate monomers. The composite also generally comprises a filler of glass, silica, crystalline, or metal oxide and a silane coupling agent to bond those components together.

In one embodiment, the composite material is comprising a polymer obtained from a bisphenol-A-glycidyl methacrylate (BIS-GMA) monomer; a triethylene glycol dimethacrylate (TEGDMA) monomers; a bis-phenol A bis (2-hydroxyethyl ether) dimethacrylate (Bis-HDMA) monomer or a combination thereof.

In one embodiment, the dental composite material is bonded to the natural tooth.

EXAMPLES

Methyl salicylate, thymol, spearmint oil, Brilliant Blue FCF, Phloxine B, Food grade isopropyl alcohol, phenol, ethyl lactate, ethyl isovalerate, betanin and hydroxy-apatite powder were purchased from Sigma Aldrich (St. Louis, Mo.). The alcoholic solvents (isopropanol and ethanol) were obtained from commercial sources, for example, ethyl alcohol was obtained from Fisher Scientific (Fisher Scientific One Reagent Lane Fair Lawn, N.J.). A chemical-cured resin cement (Concise™ Orthodontic Chemical Cure Adhesive, 3M; London, ON) was used for the preparation of composite discs and composite powder.

Composite Resin Disc Preparation

Disc-shaped composite specimens (3 mm thick, 5 mm diameter) were prepared by condensing the chemical-cured resin material into a transparent polystyrene mold. The chemical composition of the composite resin is summarized in Table 1 and the molecular structure of its matrix monomers are illustrated in Table 2. The composite resin was mixed as per the manufacturer's instructions, packed into the polystyrene molds and left to polymerize. After polymerization, the specimens were aged in distilled water for one week. Six discs were used for XPS surface characterization and shade measurements, while the rest were used to prepare the composite powder using an acrylic bur adapted on a straight hand piece. Composite powder was used for UV visible spectroscopy analysis, Fourier Transfer Infra-Red Spectroscopy (FTIR), Raman Spectroscopy.

Teeth Collection and Preparation

Extracted teeth were collected from adult patients, who attended McGill Undergraduate Dental Clinic, with dental conditions that required tooth extraction after obtaining approval from McGill University Health Center Ethical Committee and the signed informed consent from the patients. After extraction, teeth were immersed in 10% formalin solution (BF-FORM, Fisher Scientific, Ottawa, ON) for 1 week. The specimens were then cleaned with distilled water (DW) in an ultrasonic bath (FS20D Ultrasonic, Fisher Scientific, Ottawa, ON) for 60 minutes at 25° C. and polished for 1 minute with a low-speed dental hand piece (M5 Pa, KAB-Dental, Mound Road Sterling Heights, Mich., USA) using SiC cups (Pro-Cup, sds Kerr, Italy) and dental prophylaxis pumice of low abrasive capability (CPR™, ICCARE, USA). Then, the teeth were rinsed again in an ultrasonic bath before storing them in labelled Eppendorf tubes with 10% formalin solution. Post-storage, the teeth were cleaned with water and air-dried. Each tooth surface was first etched with phosphoric acid gel (3M Unitek Concise Etching Liquid; 3M Center, St. Paul, Minn.) for 30 seconds, rinsed with distilled water and air-dried. Chemical-cured adhesive (3M Unitek Concise Ortho Bond; 3M Center, St Paul, Minn.) was then mixed and applied to the tooth surface and allowed to set. The chemical-cure resin described in table 2 (below) was then mixed and applied to the base of a bracket that was then positioned on the tooth surface. The composite resin was then allowed to set. After one week of storage in a wet environment, brackets were de-bonded and composite resin was stained.

Clinical Cases

After obtaining the ethical approval from McGill University Health Center Ethical Committee and the signed informed consent from the patients the composite disclosing agent was tried to those patients. Orthodontic brackets were de-bonded and teeth were polished with a low-speed dental hand piece using SiC cups and dental prophylaxis pumice of low abrasive capability fine pumice. The required tooth was isolated using rubber dam and then the staining agent was applied to the surface of the composite resin using the same protocol that was used for staining the composite discs.

TABLE 1

Chemical composition of the composite resin used in this study presented as wt/wt % (information provided by the respective manufacturer).

| Material | | Monomer type | % | Initiator | Filler |
|---|---|---|---|---|---|
| Concise™ Orthodontic Chemical Cure Adhesive | Paste 1 | Bis-GMA | 10-20% | none | Silica <2% |
| | | TEGDMA | 1-10% | | Quartz 75-85% |
| | Paste 2 | Bis-GMA | 10-20% | BP <.5% | Silica <2% |
| | | TEGDMA | 1-10% | | Quartz 70-80% |

Abbreviations: Bis-GMA, bisphenol A glycol dimethacrylate; TEGDMA, triethylene glycol dimethacrylate; BP, benzoyl peroxide.

TABLE 2

Chemical composition of the composite resin used in the clinical cases presented as wt/wt % (information provided by the respective manufacturer).

| Material | Monomer type | % | Initiator | % | Filler |
|---|---|---|---|---|---|
| 3M Unitek Transbond XT light cure adhesive | Bis-GMA | 10-20% | camphorquinone | 0.2-0.7% | Silica <2% |
| | Bis-HDMA | 5-10% | Tertiary amine | | Quartz 70-80% |

Abbreviations: Bis-GMA, bisphenol A glycol dimethacrylate; Bis-HDMA, bis-phenol A bis (2-hydroxyethyl ether) dimethacrylate Measurements UV Visible Spectroscopy To analyze how the different tested molecules (methyl salicylate, thymol and spearmint oil) interact with composite and the tooth structure UV Visible spectroscopy was used. Dilute solutions of the three tested molecules were prepared. Methyl salicylate and thymol were dissolved in 27% ethyl alcohol whereas spearmint oil was only soluble in 100% alcohol. The resulting solutions were analyzed in triplicates using UV visible spectrophotometer (Evolution 200 series, Thermo Scientific, Madison, USA) and the resulting absorbance peaks were plotted as control (FIG. 1). After this, equal weights of composite resin and hydroxy-apatite powders were added to equal volumes of the diluted solutions of the three tested molecules. The supernatant was then further analyzed and the resultant peaks were plotted as shown in FIG. 1.

Neither the composite resin nor the hydroxy-apatite exhibited changes to the main absorbance peak of spearmint oil.

The absorbance peak for both methyl salicylate and thymol exhibited changes after the addition of 0.5 g Bis- GMA powder so further analysis using UV Visible spectrophotometer and other weights of composite resin and hydroxy-apatite (0.3, 0.8 g) was undertaken and their effect on the main absorbance peak and the percentage of absorbance of both molecules was plotted as shown in FIG. 2.

Increasing the weight of composite resin used decreased the main absorbance peak of both methyl salicylate and thymol.

Fourier Transform Infrared Spectroscopy (FTIR), Raman Spectroscopy

The FTIR analysis was carried out using an FTIR spectrometer (PerkinElmer, Liantrisant, UK). The measurements were operated in the mid-infrared range from 400 $cm^{-1}$ to 4000 $cm^{-1}$. The resulting data was analyzed using Spectrum software (version 10.3.8).

Raman spectra were collected using Senterra, Bruker, Karlsruhe, Germany, coupled to an Olympus microscope and equipped with a 785 nm (diode) laser source. The microscope was set to a 10× objective with a spot size of approximately 20 μm. A resolution of 3-5 $cm^{-1}$ was set, and spectra collection times were set to 30 s with 2 co-additions. The collected spectra were baseline-corrected using the OPUS9 7.0.0 software, Bruker, Karlsruhe, Germany.

Powders of both hydroxy-apatite and the composite materials were used for this analysis which aimed at further characterizing the chemical composition and functional groups of both materials before and after the addition of methyl salicylate solution (0.06% in 27% ethyl alcohol), and after the addition of the staining agents (1:1 mixture of Brilliant Blue FCF and Philoxine B dyes). Powders were first analyzed without any treatment, then equal weights were introduced into 6 different beakers; 3 for composite resin powder and three for hydroxy-apatite powder. Equal volumes of dilute methyl salicylate solutions were introduced into those beakers. They were left for one minute then the powders of both materials were filtered, and washed using distilled water. They were allowed to dry on filter paper then were collected for further analysis. This group was called MeSa treated. After the analysis, those MeSa treated powders were treated using the staining agent. They were left for one minute then washed, filtered and dried for further analysis. This group was called DA treated.

Surface Elemental Composition: X-Ray Photoelectron Spectroscopy (XPS)

A monochromatic X-ray photoelectron spectrometer K Alpha (Thermo Fischer Scientific Inc, East Grinstead, UK) was used to determine the surface chemical composition of all composite resin discs. Survey scans were obtained over the range of 0-1350 eV with pass energy of 200 eV at a step of 1.0 eV; high resolution (C1s, O1s, Si2p) scans were collected with pass energy of 50 eV at a step of 0.1 eV. A flood gun was used to neutralize the surface charge build-up. The binding energy (BE) scale for the specimens was calibrated by setting the value of the carbon bonded to hydrogen or carbon (C—(H, C)) as a reference at 284.8 eV. Data analysis and peak fitting were performed using the Avantage (4.60 V) analysis software.

Six composite discs were prepared for XPS analysis. Each composite disc was read at three different points; these samples were called control group. 0.06% methyl salicylate solution in 27% ethyl alcohol was applied to the composite discs using a cotton pellet. The discs were air dried after one minute, then washed using distilled water, and air dried again. Those specimens were analyzed using XPS. Each sample was read at three different points and were called MeSa samples. After this, the staining agent was added to the surfaces of the MeSa treated composite discs using a cotton pellet, the discs were air dried and washed using distilled water then dried again. Those samples were further analyzed using XPS and were called MeSa+DA samples.

Staining Procedure and Shade Measurement

The staining procedure was performed on composite resin discs, the remaining resin adhesive after de-bonding orthodontic brackets and the surrounding tooth structure following similar steps. 0.06% (v/v) methyl salicylate in 27% (v/v) ethyl alcohol was topically applied to all three types of surfaces. After waiting for one minute, it was air dried for 30 seconds then washed with distilled water and dried again. The staining agent was then applied following the same steps. Those samples were used for XPS analysis and shade measurements. The inventors also used isopropanol in the clinical cases. The solution was prepared in the same manner as for ethanol (27% V/V) and then added the methyl salicylate to form a 0.06% solution which was used for the clinical cases. The results are not displayed in the figures, however the isopropanol composition gave the same results (change in color) as the one obtained on composite discs.

Baseline shade parameters were registered using the spectrophotometer (Easy Shade®, Vita Zahnfabrik, Germany) to the six composite discs using a white background. Before each measurement session, the colorimeter was calibrated per the manufacturer's recommendations. Each reading was repeated three times and the average reading was calculated. Shade registration was repeated after both staining steps. The shade data was collected based on the percentile units of Munsell's color system (Lightness, Chroma and Hue) in which C represents Chroma which is the degree of color saturation (e.g. red to pink); and Hue (H) is the term used to describe different families of color (i.e. red, yellow, green, etc.) whereas the lightness (L) represents the brightness of a color and it ranges from Zero (black) to 100 (white). The a* and b* which are components of the CIE lab (International Commission on Illumination) besides L were also recorded. In this system, a* represents the red-green axis in which a positive a* indicate a shift to red, and the negative value indicate a shift to green. Similarly, b* the yellow-blue axis, in which a positive b* value indicates the yellow color range and a negative value indicates a blue color.

Only methyl salicylate as a representative of phenolic residue and Philoxine B and Brilliant Blue FCF were used for this part. The other tested molecules (Thymol, Phenol, Spearmint, Ethyl Lactate, and Ethyl Isovalerate) and Betanin as a dye were only assessed visually for the difference in shade.

Data Analysis

The statistical analysis was performed using SPSS software (version 22; SPSS Inc, IBM corporation, Chicago Ill.) and Origin (version 9; Origin Laboratory, Northampton, Mass., USA). All XPS and shade measurement data was presented as average and standard deviation. Normality test was carried out for all acquired data. All data representing a normal distribution was analyzed using One Way ANOVA test, whereas, otherwise Friedman Test was used and post hoc was run for statistically significant results using Wilcoxon signed-ranks with Bonferroni adjustment. The statistical significance was set at $p<0.05$.

Results

Interaction of Molecules with Composite Resin and Hydroxy-Apatite.

FIG. 1 shows the UV-vis spectrum of dilute solutions of methyl salicylate, thymol, and spearmint oil before and after the addition of 0.5 g of composite resin and hydroxy-apatite powders. The spectrum of methyl salicylate contains three peaks centered at 205, 235 and 306 nm in agreement with previous UV-vis studies. These bands arise from (π-π*) transition of the benzene ring. Thymol shows a featureless absorption band at ~225 nm and a sharp peak around 271 nm corresponding to the phenol group, while spearmint oil shows an intense broad band from 200 to 275 nm and a weak band from 325 to 350 nm. The observed UV spectrums suggest that these compounds can absorb UV light due to the presence of either or both conjugated pi (π)-bonding systems (π-π* transition) and nonbonding electron system (π-π* transition).

The addition of composite resin to dilute solution of methyl salicylate decreases the main absorbance peak of methyl salicylate at 306 nm by 37±3.9%, 38±25%, 85±12% for 0.3, 0.5, and 0.8 g, respectively, whereas minimal change in spectrum was observed when HA was added to MeSa (13±22%, 11±14%, and 1.1±15% for 0.3, 0.5, and 0.8 g hydroxy-apatite, respectively. Similarly, the addition of composite resin to dilute thymol solution decreases the main absorbance peak at 272 nm by 47±17%, 55±1.2%, and 66±2.9% for 0.3, 0.5, and 0.8 g, respectively. In contrast, hydroxy-apatite lead to minimal changes; 14±3.3%, 10±9.2% and 7±1.6% for 0.3, 0.5, and 0.8 g of hydroxy-apatite, respectively. As for spearmint, no changes were noted to the main absorbance peak after the addition of either composite resin and hydroxy-apatite.

Surface Chemical Analysis of Samples

FIG. 3 shows FTIR spectra for both composite resin and hydroxy-apatite powders before and after the addition of methyl salicylate and after the addition of staining agent. All spectra of control and treated resin composite (FIG. 3a-c) displayed two small peaks at 2890 cm$^{-1}$ and 2930 cm$^{-1}$ characteristic for the symmetric and asymmetric C—H stretching vibrations of the methyl groups. The peaks at 1604 cm$^{-1}$ and 1720 cm$^{-1}$ correspond to C═C stretching vibration and the carbonyl (C═O) stretching respectively of the polymeric constituent present in the composite powder. The peaks at 1558 and 1457 cm$^{-1}$ are most probably the skeletal vibrations of the benzene ring. The broad band around 930-1225 cm$^{-1}$ showed asymmetric stretching of C—O—C and Si—O stretching vibration due to presence of silicates in the constituents. The addition of methyl salicylate (MeSa) to resin composite increases the intensity of the C—H bands between 2846-3027 cm$^{-1}$ and causes some changes in the IR spectrum around 1450 cm$^{-1}$ corresponding to the skeletal vibrations of the benzene ring. This behavior could indicate the interactions between the MeSa and the resin composite.

As expected, the FTIR spectra of Hydroxy-apatite control and after the treatment with methyl salicylate and staining agent (FIG. 3 d-f) show their main components, namely $PO_4^{3-}$ and $CO_3^{2-}$. Indeed, $PO_4^{3-}$ group forms intensive IR bands at 560 and 600 cm$^{-1}$ and at 1000-1100 cm$^{-1}$, whereas $CO_3^{2-}$ group forms weak peaks between 870 and 880 cm$^{-1}$ and between 1460 and 1530 cm$^{-1}$. There is no change in the FTIR spectrum of Hydroxy-apatite before and after the two-step treatment which would indicate that the MeSa does not react with the Hydroxy-apatite.

Figure 3A:
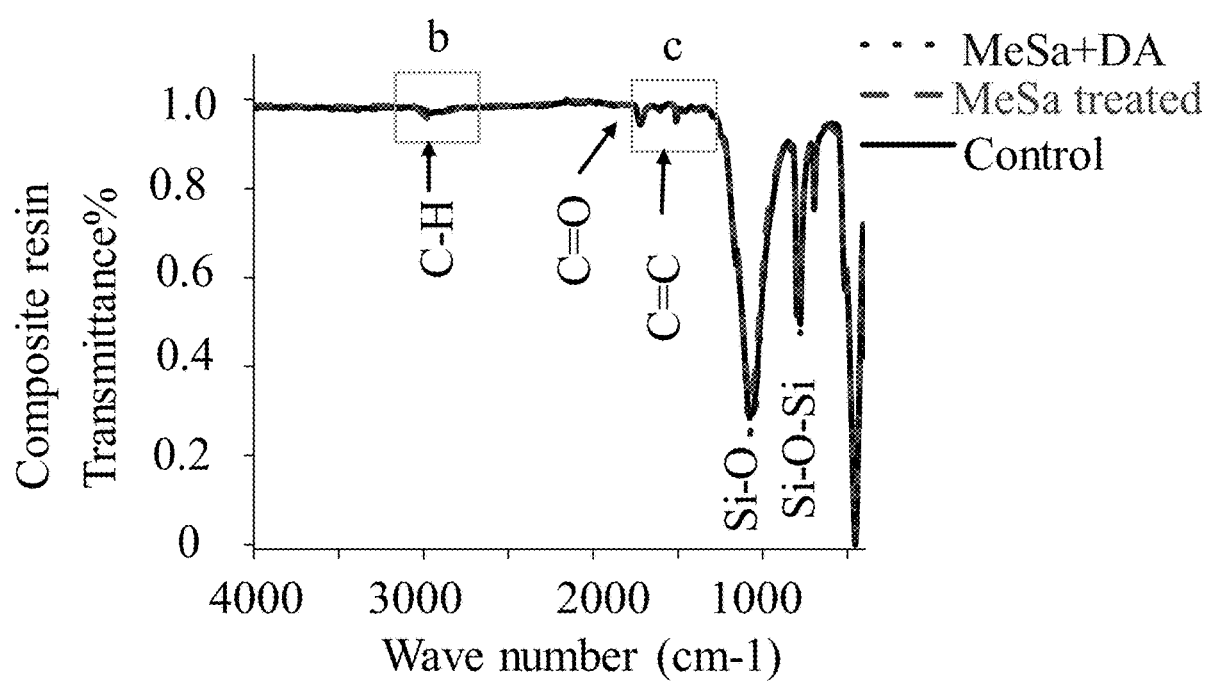
FIG. 3(a) is a FIR spectrum for a composite resin for control powders and after the addition of 0.06% methyl salicylate (MeSa treated) and after the addition of staining agent (MeSa+DA)
Figure 3B:
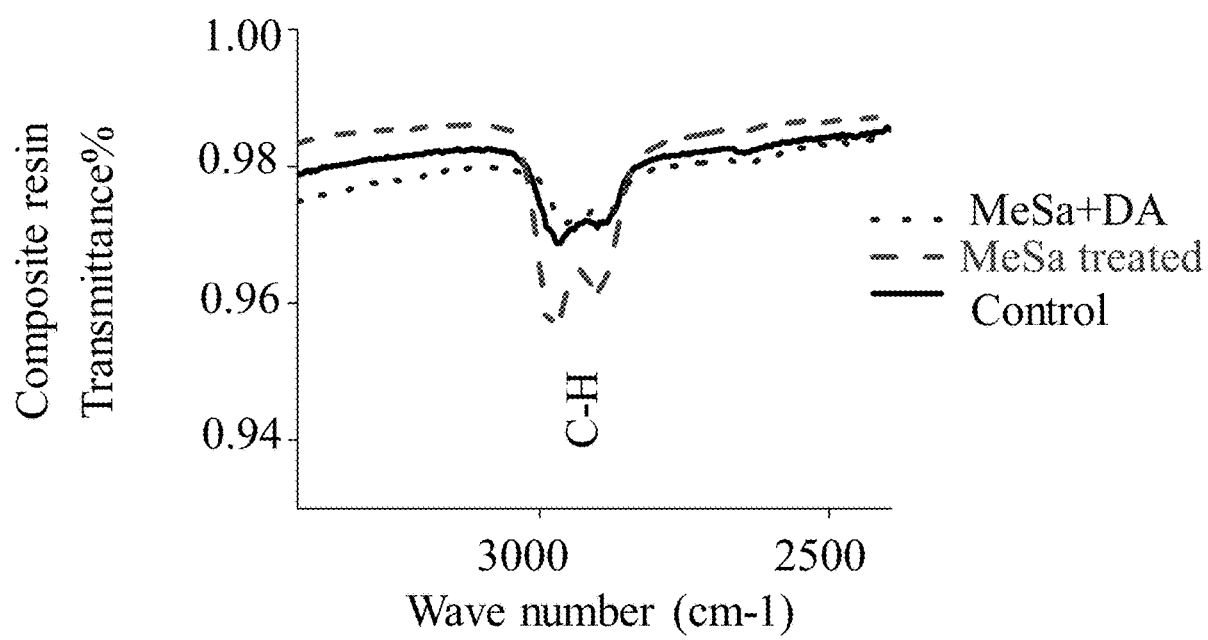
FIGS. 3(b) and 3(c) represent zoom in areas in the FTIR spectrum of the composite resin of FIG. 3(a)
Figure 3C:
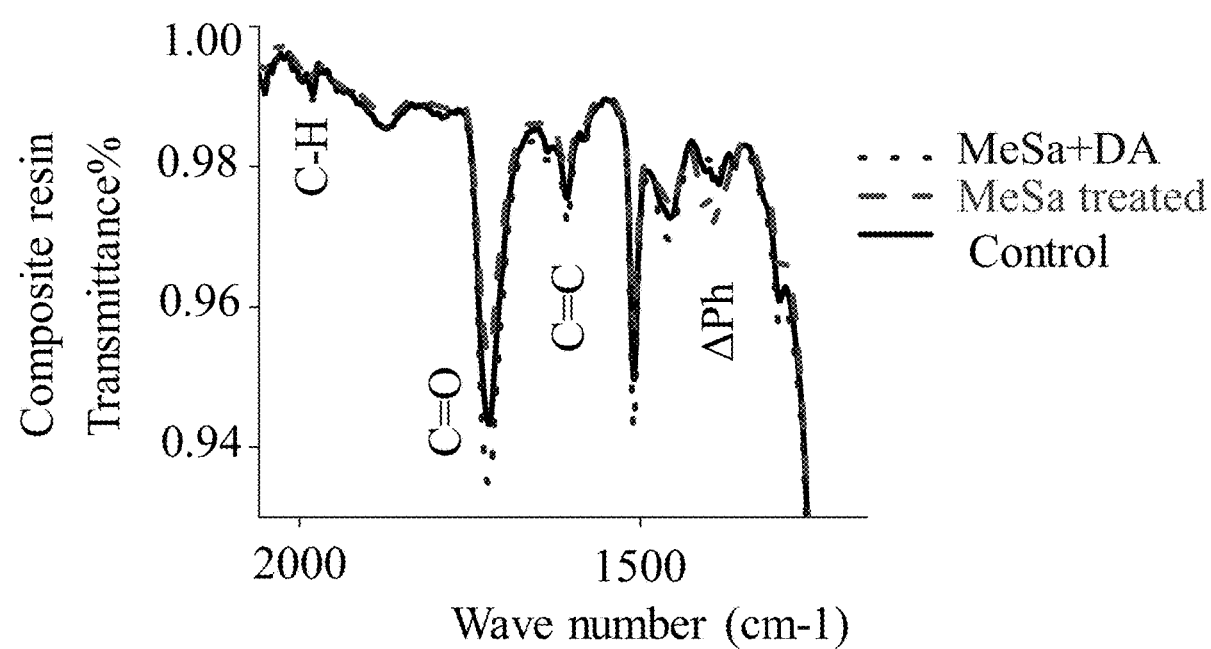
Figure 3D:
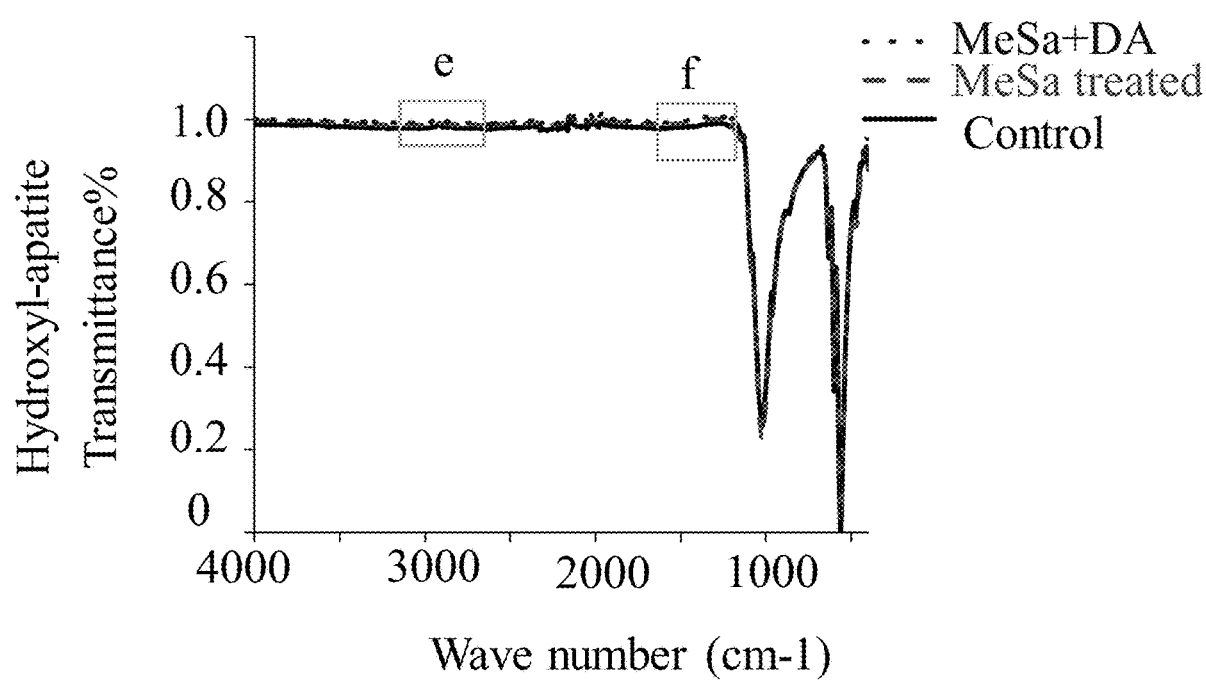
FIG. 3(d) is a FIR spectrum for hydroxy-apatite for control powders and after the addition of 0.06% methyl salicylate (MeSa treated) and after the addition of staining agent (MeSa+DA)
Figure 3E:
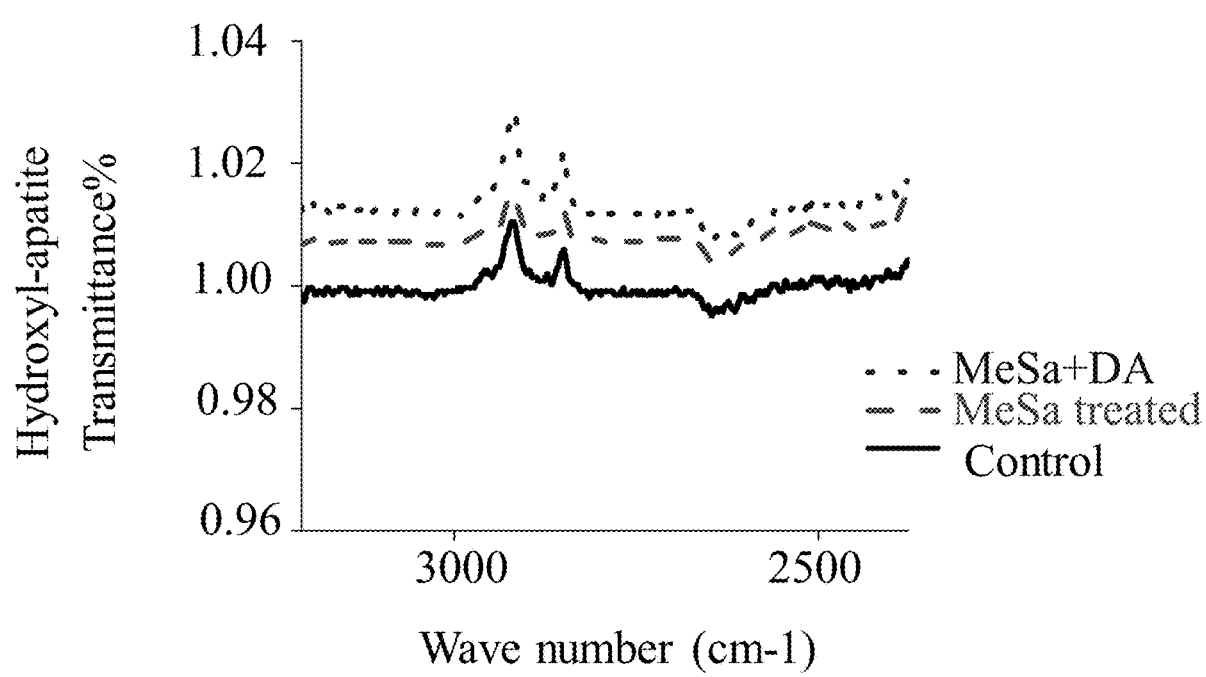
FIGS. 3(e) and 3(f) represent zoom in areas in the FTIR spectrum of hydroxy-apatite of FIG. 3(d)
Figure 3F:
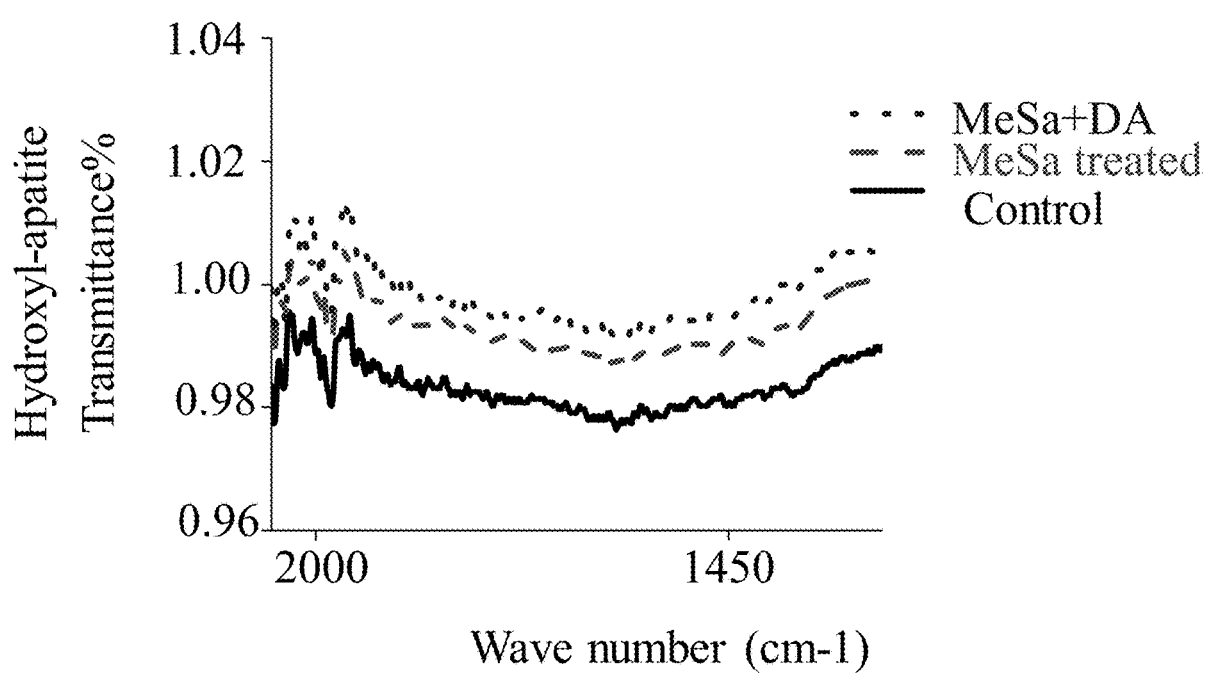
Figure 4A:
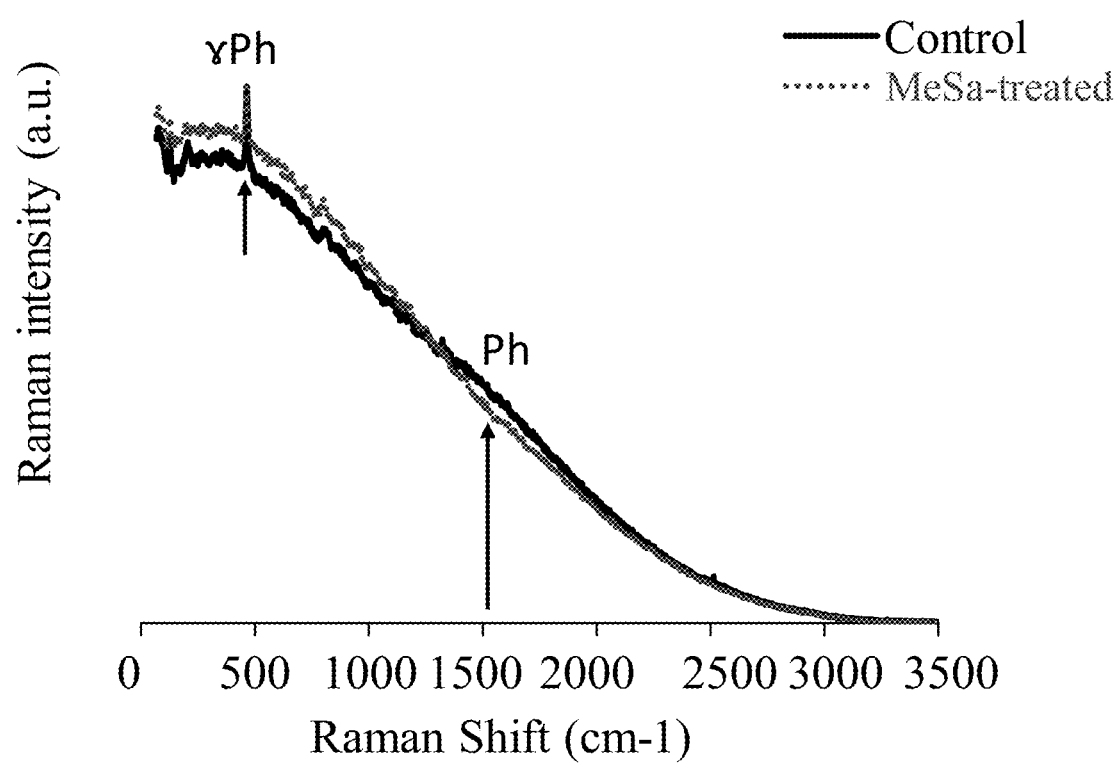
FIG. 4(a) is a Raman spectrum for a composite resin both for control powders and after the addition of 0.06% methyl salicylate.

Raman spectroscopy of composite resin and composite resin/methyl salicylate is shown in FIG. 4a. The Raman spectrum is not very informative, this possibly being due to fluorescence. Some peaks that should be seen at 2931 [v(CH)], 1716 [v(C═O)], 1639 [v(C═C)], and 1460 cm-* (skeletal vibration of the benzene nucleus) are not clearly observed. Only a tiny peak which could be assigned to phenyl-C-phenyl has been detected at 440 cm$^{-1}$. This increase in the intensity and sharpness of this peak could indicate the interaction between the methyl salicylate and the composite resin. The appearance of this peak indicates that methyl salicylate was able to react with the composite resin. This confirms the results obtained by the FTIR (FIG. 3a-c).

Figure 4B:
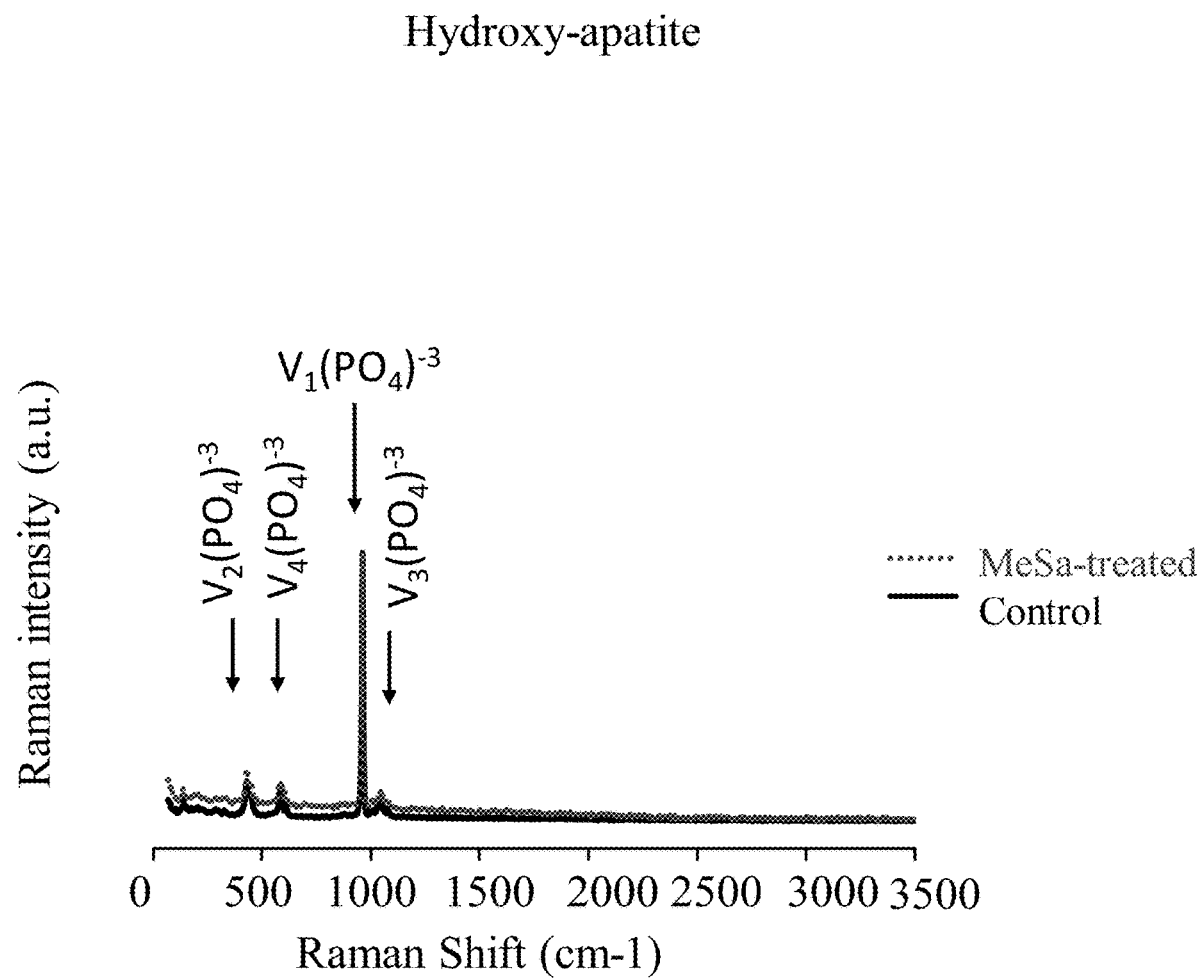
FIG. 4(b) is a Raman spectrum for hydroxy-apatite both for control powders and after the addition of 0.06% methyl salicylate.

Raman spectra of hydroxy-apatite and hydroxy-apatite/MeSa is shown in FIG. 4b. The internal modes of the $PO_4^{3-}$ tetrahedral $v_1$ frequency (961 cm$^{-1}$) correspond to the symmetric stretching of P—O bonds. The vibrational band at 439 cm$^{-1}$ ($v_2$), is attributed to the O—P—O bending modes. The band present at 1050 cm$^{-1}$ ($v_3$) corresponds to asymmetric v3 (P—O) stretching. The $v_4$ frequency (602 cm$^{-1}$) can be assigned mainly to O—P—O bending. These bands are characteristic of crystallized apatite phase. No change is detected in the FT-Raman spectrum after the addition of MeSa as indicated in FIG. 4b, which indicates that MeSa does not react with the Hydroxy-apatite and this confirms the IR results.

Figure 5A:
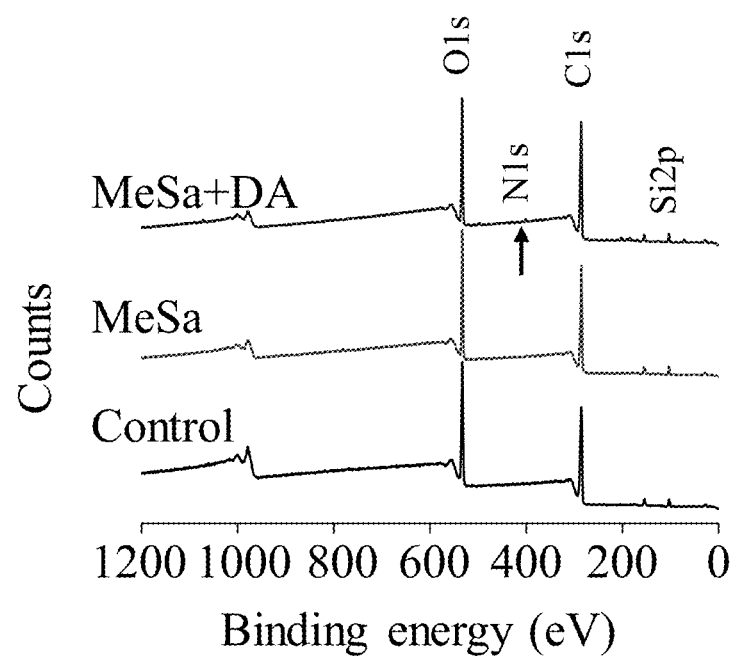
FIG. 5(a) is an XPS general survey of composite resin discs for control, after the addition of methyl salicylate (MeSa), and after the addition of the staining agent (MeSa+DA)
Figures 5B, 5C:
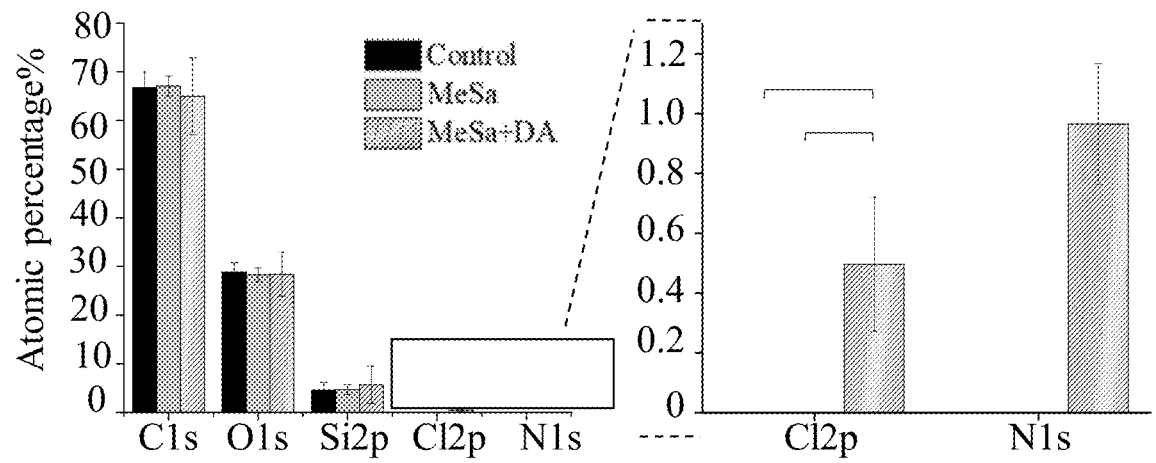
FIG. 5(b) is a quantitative elemental composition analysis of composite resin discs for control, after the addition of methyl salicylate (MeSa), and after the addition of the staining agent (MeSa+DA)
FIG. 5(c) represents a zoom in areas of FIG. 5(b). Data analyzed using One Way ANOVA and Kruskal-Wallis tests at a significant level p<0.05. Brackets indicate statistically significant differences between groups.
Figures 6A, 6B:
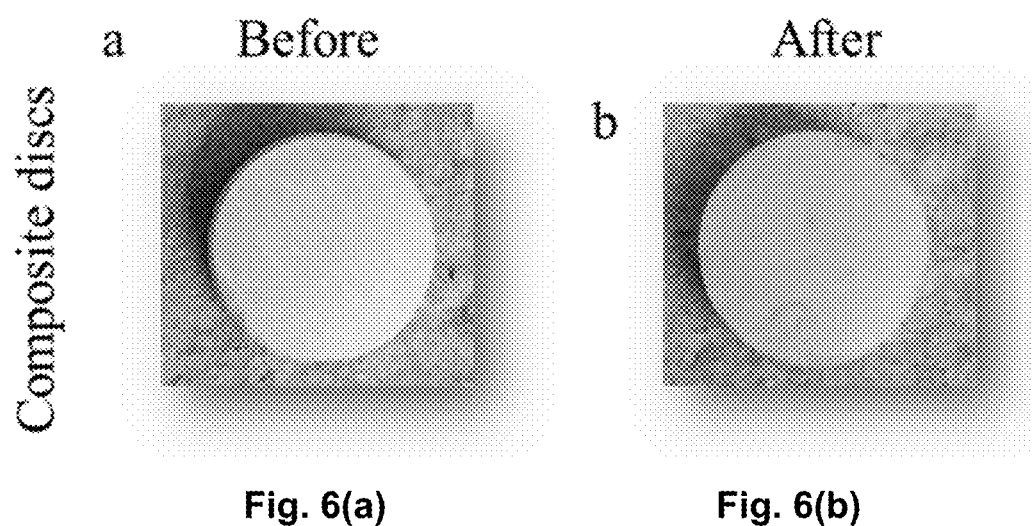
FIGS. 6(a) and 6(b) are digital photographs showing resin composite discs (a) before and (b) after the two step staining procedure described herein.
Figures 6C, 6D:
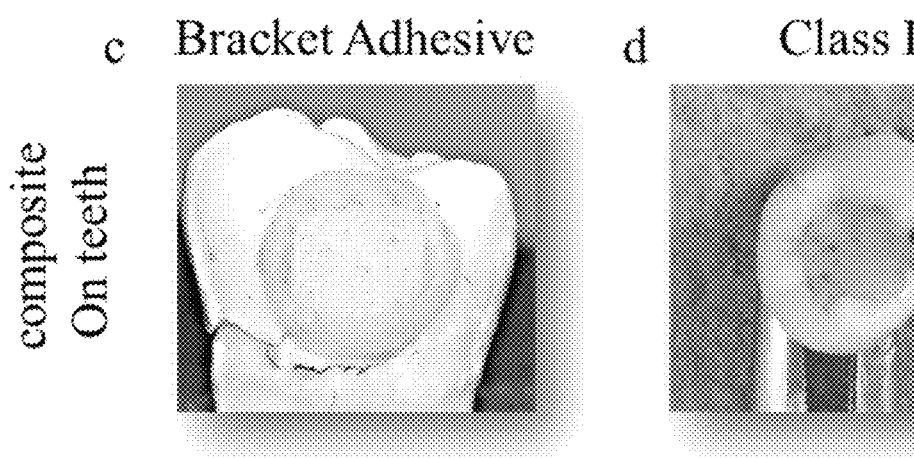
FIG. 6(c) and FIG. 6(d) are digital photographs of tooth that has (c) stained resin based adhesive after de-bonding orthodontic brackets, and (d) stained class I composite filling.

FIG. 5 represents the XPS analysis of the control (non-treated resin), MeSa treated, and MeSa+ staining agent treated. All spectra show similar atomic percentages of C1s with an average of 66.7±3.2%, 67.1±2.1% and 65.0±8.0%, O1s with an average of 28.8±1.9%, 28.2±1.4%, and 28.4±4.5%, and Si2p 4.6±1.6%, 4.7±1.0%, and 5.7±3.8% for control, MeSa and MeSa+ staining agent specimens respectively. Interestingly, in contrast to control and MeSa treated groups, the treatment with disclosing agent results in detectable peaks at 198.5 eV (0.5±0.2%) and 398.1 eV (1.0±0.2%) attributed to C12p and N1s respectively. Data analyzed using One Way ANOVA and Kruskal-Wallis tests at a significant level p<0.05. Brackets indicate statistically significant differences between groups To gain further information on the chemical environment of surface atoms, we recorded high resolution C1s and O1s (FIG. 6). The high resolution C1s peak was de-convoluted into three components. A peak at 284.8 eV attributed to both aliphatic and aromatic hydrocarbons (C—C/C—H) and two peaks at 286.3 eV and 288.6 eV assigned to the carbon-oxygen functionals C—O and C═O respectively. XPS Results showed that no significant change is observed in these components after treatment with the Mesa and the MeSa+ staining agent. In fact, we measured the atomic percentages of 63.7±3.7, 62.9±1.6 and 62.2±2.3 for C—C and 27.6±2.6, 28.1±1.4 and 28.5±1.8 for C—O and 8.8±1.6, 8.9±0.3, 9.3±0.9 for C═O for control, MeSa and MeSa+ staining agent treated groups respectively (FIG. 6). The high resolution O1s peak was de-convoluted into three peaks. A main peak at 532.5 assigned to O—Si and two lower peaks at 531.2 eV and 533.5 eV attributed to O═C and O—C respectively (D. Briggs, et al. XPS studies of the oxygen 1s and 2s levels in a wide range of functional polymers, Analytical Chemistry 65(11) (1993) 1517-1523;

G. P. López, et al. XPS O 1s binding energies for polymers containing hydroxyl, ether, ketone and ester groups, Surface and interface analysis 17(5) (1991) 267-272).

The concentration of these components was not significantly different for the control, MeSa and MeSa+ staining agent treated specimens. The measured atomic concentrations were 18.6±10.7, 14.4±8.9, 18.1±8.9 for O═C, 58.8±7.4, 59.0±2.8, 60.0±6.4 for O—Si, and 22.5±7.4, 26.6±7.6, 21.8±6.3 for O—C for control, MeSa and MeSa+ staining agent samples respectively.

Shade Measurements

Figure 6E:
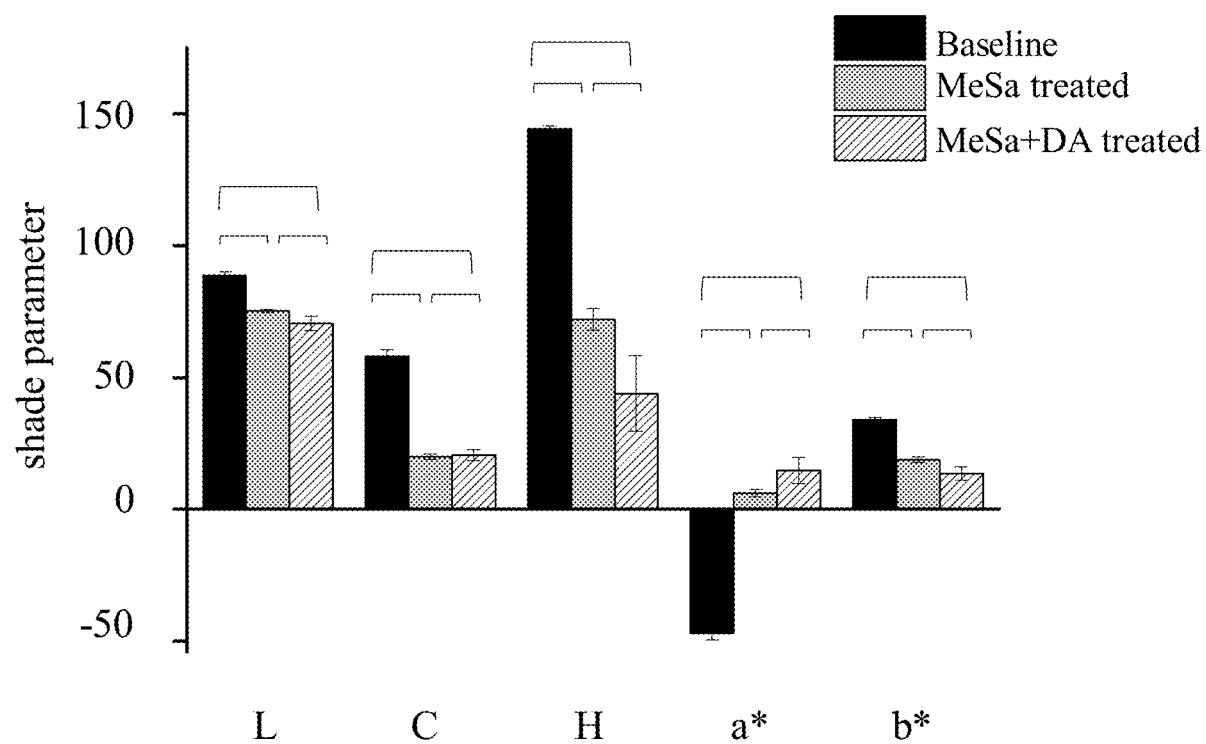
FIG. 6(e) represents changes in shade parameters recorded as average and standard deviation for control (at baseline), after treatment with methyl salicylate solution (MeSa), and after the addition of the staining agent to primed samples (MeSa+DA). Data analyzed using One Way ANOVA at a significant level p<0.05. Brackets indicate a statistically significant differences between groups.

Results of shade measurements indicate success of the new composite resin disclosing process. FIG. 6 shows photos of stained composite resin discs before and after staining with the new composite disclosing process, and photos of stained composite resin on teeth. The results of shade measurements (FIG. 6e) indicate a statistically significant difference for all shade measurements from baseline. Those results were further confirmed by the two clinical cases which indicated that the two-step composite disclosing process successfully stained resin-based adhesive after bracket de-bonding making it more visible and easier to be cleaned from the tooth structure.

This specification characterizes the interaction between composite resin and different molecules which resulted in the development of a composite disclosing process comprising a phenolic residue-containing compound such as methyl salicylate, an FDA approved food flavoring (T. R. E. Panel, et al. A toxicologic and dermatologic assessment of salicylates when used as fragrance ingredients, Food and Chemical Toxicology 45(1) (2007) S318-S361), and a staining agent (such as Brilliant Blue FCF and Philoxine B). This technology would help the dental practitioners to easily identify the boundaries of composite restorations and save them the stress and inconvenience with this tedious procedure.

Methyl salicylate, thymol, and spearmint oil were chosen for the first staining step. All molecules are FDA approved, registered food additives and in use as flavoring agents. Methyl salicylate is also used as a topical analgesic for the treatment of muscular and rheumatic pain, and in Listerine mouthwash. Both methyl salicylate and thymol have an ortho-substituted phenol group. Methyl salicylate is also well known for its intramolecular hydrogen bond between the phenolic hydroxyl group (proton donor) and the carboxyl group (proton acceptor). Methyl salicylate was able to interact more with the composite resin as indicated by the results of the UV visible spectroscopy this is why it is chosen to pre-treat the composite resin and in the development of the composite staining agent. This concentration was chosen being the concentration already in use in Listerine™ mouth wash and in this study this concentration proved enough.

Interaction with Composite Resin and the Tooth Structure.

The characterization of the interaction between the staining components and both composite resin and the tooth structure was performed using UV visible spectroscopy which was chosen to characterize indirectly the insoluble powder; a method that is largely used in pharmaceutical industry. In this method, different weights of insoluble polymer are added to a known concentration of a solute with a clear fingerprint in UV-vis spectrum. After each addition, the filtered solutions are then analyzed using UV-vis spectrophotometer and the resultant effect on the UV spectrum is compared to the baseline readings.

In this study, the calibration curve shows that the concentration of 0.06% provides a maximum absorbance of 1.1 at $\lambda_{max}$=307. The analysis of the supernatant of MeSa solution after the addition of different weights of composite resin and hydroxy-apatite powder reveals a decrease in this absorbance peak as composite resin mass increased whereas no change occurs in case of HA. This observation indicates a preferential adsorption of MeSa on resin surface likely due to π-π interaction and hydrogen bonding between MeSa and the polymeric components of the resin. According to Beer Lambert's Law absorbance of light is related to the concentration of material in solution and thus the decrease of absorbance could be related to the extent of interactions between the solute and the polymer. The addition of different weights of composite resin to thymol solution resulted in similar changes to the UV spectrum observed in methyl salicylate which proves our hypothesis, nevertheless, its interaction with hydroxy-apatite makes it not suitable to be used as a composite disclosing agent. This has probably happened because thymol is more hydrophilic than methyl salicylate and has better solubility in water and the tooth enamel can be stained by hydrophilic stains.

Spearmint oil has poor solubility properties. It is only soluble in 100% alcohol. Furthermore, it had no effect on the absorption spectrum of either composite resin or hydroxy-apatite. methyl salicylate was more suited as no interaction existed with hydroxy-apatite thus analysis was resumed only with methyl salicylate.

For the second staining step 1:1 concentration of two food dyes was chosen. Both molecules (Brilliant Blue and Philoxine B) are rich in aromatic rings, we believe it could interact with the methyl salicylate molecule and thus was successful in staining composite through the pi-pi interaction mechanism.

The interaction of methyl salicylate with composite resin and not hydroxy-apatite was further confirmed by IR spectroscopy. Indeed, the addition of methyl salicylate to the composite resin increases the intensity of the C—H (FIG. 4b) and C=C peaks (FIG. 4c). This indicates a change in the concentration of these functional groups supporting thus the adsorption of MeSa to the resin composite. In contrast IR spectrum for hydroxy-apatite had no change in absorbance at the C—H region after the addition of methyl salicylate.

XPS shows that the atomic percentages of (C, O and Si) did not exhibit marked changes. This could be attributed to the low concentration of methyl salicylate in solution, besides the fact that both composite resin and methyl salicylate have the same atoms in their structure (C, O, H). It could also be anticipated that part of the adsorbed molecules was lost during washing and air-drying procedure after each staining step. Nevertheless, Cl and N atoms were present in small atomic percentages (0.49, 0.96 respectively) after the second staining step which proves the presence of staining agent on treated composite specimens (FIG. 5). The high resolution O1s peak was recorded to confirm the presence of the new disclosing agent on the composite discs' specimens. Although the change in the O—C and O=C bonds did not exhibit statistically significant changes, the atomic percentage of O—C bond increased after the addition of methyl salicylate and this confirms the presence of methyl salicylate as it contains C—O, C—OH bonds the peaks of which overlap towards the higher binding energy (peak presented as O—C in the atomic percentages and the graph in FIG. 5f). After the addition of staining agent the atomic percentages of both O—C and O=C decreases likely to the shielding effect of the staining agent over layer.

Efficiency of the New Disclosing Agent

The most important test that confirms the efficiency of the new composite disclosing agent is its being visible under conventional visible light and its ability to stain composite and not the tooth structure. Composite resin is found to be more hydrophobic than the tooth structure, accordingly there is a difference in their susceptibility to being stained. Using our new 2-step staining protocol, composite resin was stained pink whereas the tooth structure did not exhibit any marked visual changes as shown in FIG. 6. To quantify the difference in shade before and after the straining steps we used Easy shade Vita spectrophotometer due to its high precision among color measuring devices. All five recorded shade parameters showed significant changes between the three tested groups. L value significantly decreased; this indicates that the specimen became darker. As for the a* parameter, it has changed from negative value in control specimens to a positive value after both staining steps. This indicates that the color of our specimen has shifted towards the red axis. Similarly, there was a shift towards the blue axis for the b* value which was clear as a statistically significant decrease in the b value for treated specimens. A significant change was also noted in both C and h values. As for hue the readings have changed from bluish green area to yellowish after the addition methyl salicylate and to reddish pink after the second staining step. These changes were visible to the eye under conventional light. Similar changes were observed when we used Phenol and Thymol for the first priming step before adding Philoxine B and Billiant Blue, whereas, no changes were observed for the rest of the molecules (spearmint, Ethyl Lactate, and Ethyl Isovalerate). Similarly, Betanin was used as a negative control for the second staining step. It did not induce any visual changes in color to the resin-based adhesive primed with methyl salicylate.

All references cited herein are incorporated by reference in their entirety.

The invention claimed is:

1. A method of revealing a composite material comprising:
   a. applying a phenolic residue-containing compound to the composite material; and
   b. applying a staining agent after step a.

2. The method of claim 1, wherein said step of applying the phenolic residue-containing compound is comprising applying a solution of said phenolic residue-containing compound to the composite material and drying said solution of said phenolic residue-containing compound before applying the staining agent.

3. The method of claim 1, wherein said step of applying the staining agent is comprising applying a solution of said staining agent and drying said solution of said staining agent.

4. The method of claim 1, wherein said step of applying the phenolic residue-containing compound is comprising applying a solution of said phenolic residue-containing compound to the composite material, drying said solution of said phenolic residue-containing compound, washing said composite material with water and drying said washed composite material before applying the staining agent and wherein said step of applying the staining agent is comprising applying a solution of said staining agent, drying said solution of said staining agent, washing said composite material with water and drying said washed composite material.

5. The method of claim 1, wherein said the phenolic residue-containing compound is a mono-aromatic, topically non-toxic compound.

6. The method of claim 1, wherein said phenolic residue-containing compound is a mono-aromatic, orally non-toxic compound in a form of an ethanolic solution, the compound being non-toxic for natural tooth and having one or more of the following properties: substantially soluble in ethanol at room temperature, a MW of from about 90 to 220, and a Log P of from about 1.4 to about 5.3.

7. The method of claim 1, wherein said phenolic residue-containing compound is methyl salicylate, thymol or phenol.

8. The method of claim 1, wherein said staining agent is a food-grade dye.

9. The method of claim 1, wherein said staining agent is methylene blue, Brilliant Blue FCF or Phloxine B.

10. The method of claim 1, wherein said composite material is a dental filling composite material or an orthodontic bonding resin for brackets.

* * * * *